United States Patent [19]
Kroll

[11] Patent Number: 5,836,973
[45] Date of Patent: *Nov. 17, 1998

[54] STAGED ENERGY CONCENTRATION FOR AN IMPLANTABLE BIOMEDICAL DEVICE

[76] Inventor: Mark W. Kroll, 13011 Brenwood Trail, Minnetonka, Minn. 55343

[ * ] Notice: The term of this patent shall not extend beyond the expiration date of Pat. No. 5,407,444.

[21] Appl. No.: 745,724

[22] Filed: Nov. 12, 1996

Related U.S. Application Data

[63] Continuation of Ser. No. 486,760, Jan. 7, 1995, Pat. No. 5,674,248, which is a continuation-in-part of Ser. No. 993,094, Dec. 18, 1992, Pat. No. 5,407,444, which is a continuation-in-part of Ser. No. 126,044, Sep. 23, 1993, Pat. No. 5,439,482, which is a continuation-in-part of Ser. No. 93,292, Dec. 18, 1992, Pat. No. 5,383,907.

[51] Int. Cl.$^6$ ................................................. A61N 1/39
[52] U.S. Cl. ........................................................ 607/5
[58] Field of Search ............................................ 607/5, 12

[56] References Cited

U.S. PATENT DOCUMENTS 5,407,444  4/1995  Kroll ................................................. 607/5

Primary Examiner—William E. Kamm
Assistant Examiner—George R. Evanisko
Attorney, Agent, or Firm—Brad D. Pedersen

[57] ABSTRACT

A staged energy storage system provides electrical energy to an implantable biomedical device by using the combination of a first stage energy source and a second stage energy concentration system. The second stage energy concentration system allows a lower density and/or lower voltage energy source to be used as the first stage energy source, thereby decreasing the battery cost, size and weight. In one embodiment, the second stage energy concentration system comprises a rechargeable battery. In another embodiment, the second stage energy capacitor system comprises a high energy density capacitor system. The staged energy storage system is ideal for internally charging a pulse-generating capacitor system within an implantable cardioverter defibrillator. In this embodiment, a high voltage transformer has a secondary side that is electrically connected to the pulse-generating capacitor system. A second stage concentration system is electrically connected between a first stage energy source and a primary side of the high voltage transformer to store at least a portion of an electrical charge that is delivered from the first stage energy source and to the high voltage transformer.

4 Claims, 3 Drawing Sheets

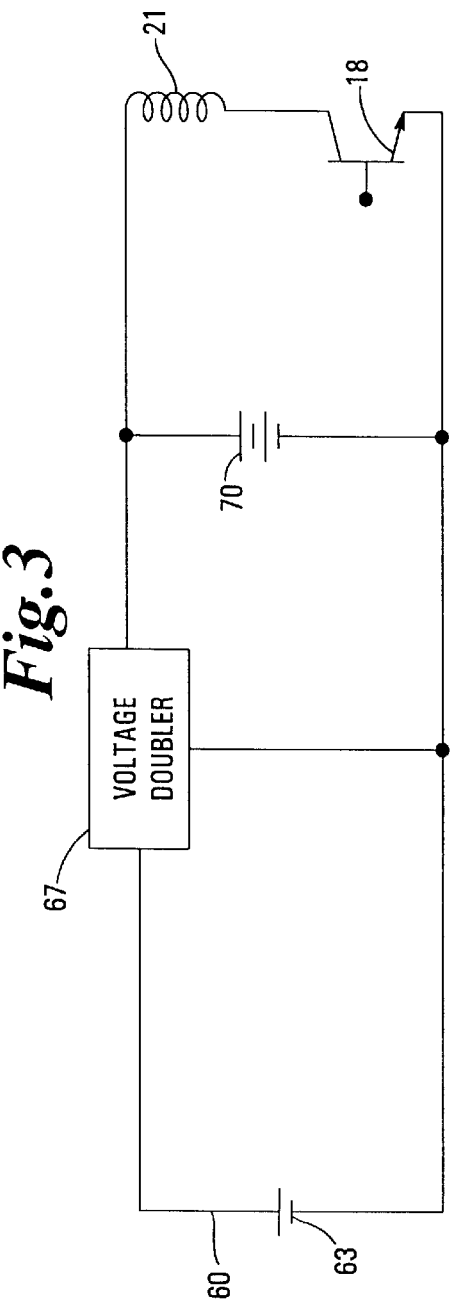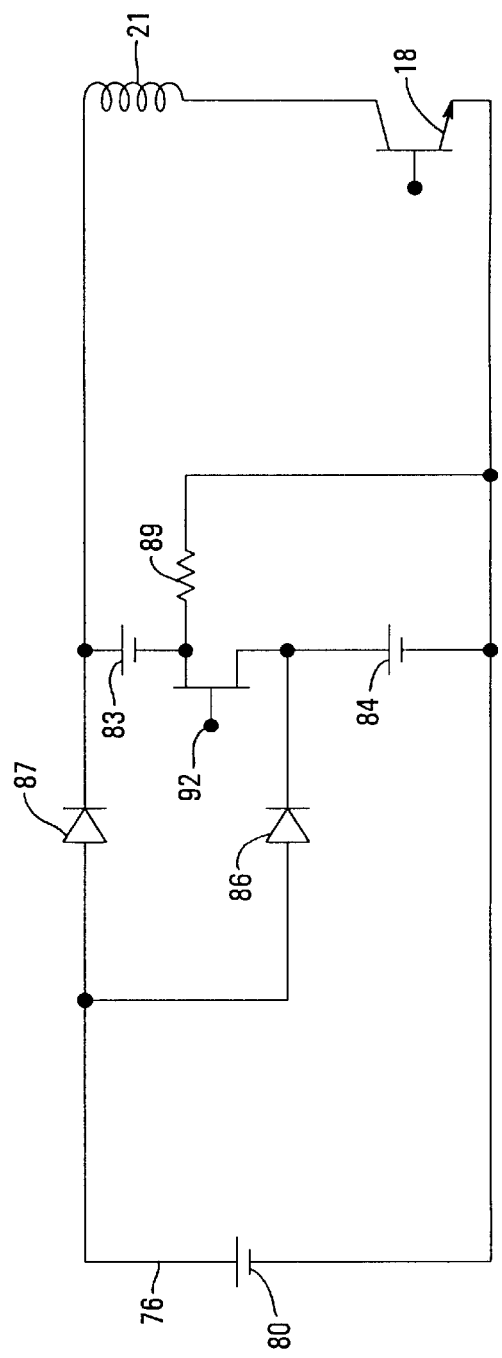

STAGED ENERGY CONCENTRATION FOR AN IMPLANTABLE BIOMEDICAL DEVICE

RELATED APPLICATIONS

This is a Continuation of application Ser. No. 08/486,760 filed Jun. 7, 1995, now U.S. Pat. No. 5,674,248, which in turn is a continuation-in-part of three applications Ser. No. 993,094 filed Dec. 18, 1992, Ser. No. 126,044 filed Sep. 23, 1993, Ser. No. 093,292 filed Dec. 18, 1992, now issued as U.S. Pat. Nos. 5,407,44, 5,439,482, and 5,383,907, respectively.

FIELD OF THE INVENTION

This invention relates to the power supply for an implantable biomedical device, and more particularly to use of a low voltage, high energy density, second stage concentration system for providing short-term high output charges for use by implantable biomedical devices.

BACKGROUND OF THE INVENTION

Implantable biomedical devices typically do not have large current requirements in order to maximize the overall useful battery life and minimize the size of the battery required to power such devices. A good example of such a low power biomedical device which utilizes only microwatts of power is a pacemaker. More recently, however, implantable biomedical devices have been developed which have higher power requirements, often in the milliwatts to watts range. Consequently, there has been a need to develop better energy storage systems for these devices that are capable of producing the level of energy needed to power a typical implantable biomedical device such as a cardioverter/defibrillator, while at the same time not creating material cost as well as weight/volume demands that would render their use impractical.

A good example of an implantable biomedical device which has a higher power output requirement is an implantable cardioverter defibrillator. Cardiac defibrillation in humans using an implantable cardioverter defibrillator requires the delivery of an electrical pulse that is several milliseconds long with peak currents as high as 25 amperes. The total energy in such a pulse can be as high as about 30–40 Joules. In order to deliver such a high current, a high voltage defibrillation capacitor system is charged up to a voltage on the order of about 750 volts and then is selectively discharged through at least a pair of implantable electrodes in the form of a defibrillation/cardioversion countershock.

Various special batteries have been developed to supply such a high current to charge the high voltage defibrillation capacitor of an implantable cardioverter defibrillator. However, the power sources used for existing implantable cardioverter defibrillators comprise relatively low energy density batteries (about 500 J/gram) which occupy a relatively large volume within the device. In addition, these special batteries are very expensive and most implantable cardioverter defibrillators require the use of two such battery cells. In implantable cardioverter defibrillator devices, the combined volume of the battery and the high voltage defibrillation capacitor(s) is greater than the electronics. Therefore, any reduction in battery cost, size or weight provides significant enhancements to an implantable cardioverter defibrillator.

SUMMARY OF THE INVENTION

A staged energy storage system provides electrical energy to an implantable biomedical device by using the combination of a first stage energy source and a second stage energy concentration system. The second stage energy concentration system allows a lower density and/or lower voltage energy source to be used as the first stage energy source, thereby decreasing the battery cost, size and weight. In one embodiment, the second stage energy concentration system comprises a rechargeable battery. In another embodiment, the second stage energy capacitor system comprises a high energy density capacitor system.

In accordance with a first aspect of the present invention, a staged energy storage system provides low voltage energy to an implantable biomedical device. A first stage energy source provides a long-term, low-voltage, low-current source of electrical charge of less than 10 mA. A second stage energy concentration system stores the long-term, low-voltage, low-current source of electrical charge delivered from the first stage energy source means. The electrical charge in the second stage energy concentration system is selectively discharged as at least one short-term, low-voltage, high-current discharge of greater than 0.5 A. The first stage energy source, the second stage energy concentration system, and the system for selectively discharging the electrical charge are all contained within the implantable biomedical device.

In accordance with a second aspect of the present invention, an improved energy storage system is provided for an implantable cardioverter defibrillator that produces a truncated capacitor-discharge countershock pulse. The implantable cardioverter defibrillator is a self-contained human implantable device including a pulse-generating capacitor system for storing an electrical charge, an energy storage system for internally charging the pulse-generating capacitor system, and circuitry for selectively discharging the electrical charge in the pulse-generating capacitor system through electrodes implanted in a human patient in response to a system for the sensing of a cardiac dysrhythmia in the human patient. The improved energy storage system includes a first stage battery energy source, a high voltage transformer and a second stage energy concentration system. The high voltage transformer has a primary side and a secondary side, the secondary side being electrically connected to the pulse-generating capacitor system. The second stage energy concentration system is electrically connected between the first stage battery energy source and the high voltage transformer, and stores an electrical charge that is delivered from the first stage battery energy source and is applied to the high voltage transformer in response to the system for the sensing of a cardiac dysrhythmia.

In accordance with a third aspect of the present invention, a staged energy storage system is provided for internally charging a pulse-generating capacitor system within an implantable cardioverter defibrillator. The staged energy storage system includes a first stage battery, a high voltage transformer and a second stage concentration capacitor system. The high voltage transformer has a primary side and a secondary side, the secondary side being electrically connected to the pulse-generating capacitor system. The second stage concentration capacitor system is electrically connected between the first stage battery and the high voltage transformer to store at least a portion of an electrical charge that is delivered from the first stage battery and to the high voltage transformer.

BRIEF DESCRIPTION OF THE DRAWINGS

FIG. 3 is a simplified schematic circuit diagram of an alternate embodiment staged energy concentration circuit.

FIG. 4 is a simplified schematic circuit diagram of an alternate embodiment staged energy concentration circuit.

DETAILED DESCRIPTION OF THE INVENTION

Figure 1:
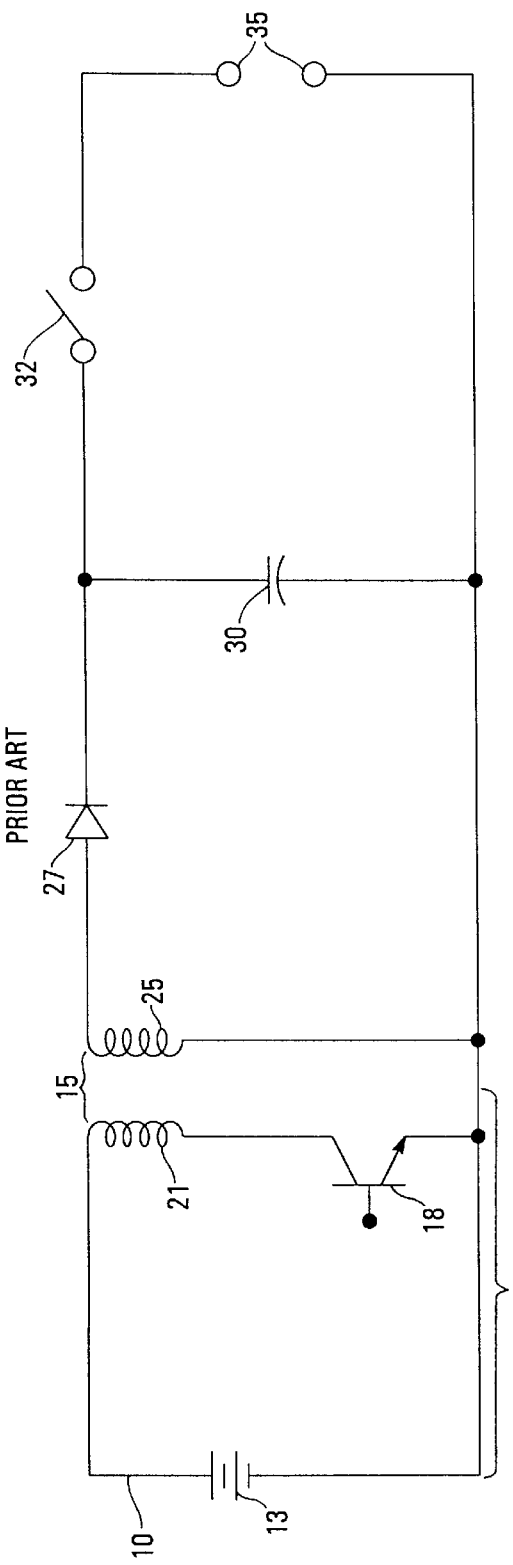
FIG. 1 is a simplified circuit diagram of a prior art implantable defibrillator circuit.

FIG. 1 is a simplified circuit diagram of a known implantable defibrillator circuit 10. Circuit 10 comprises a high current defibrillation battery 13, which is typically a low energy density lithium silver vanadium oxide (SVO) battery. A high voltage transformer 15 comprises a transistor switch 18 which drives the primary 21. The oscillator driving switch 18 provides an alternating current through the primary of transformer 15. The secondary 25 of transformer 15 produces a significantly higher voltage which is rectified by diode 27 and stored in high voltage defibrillation capacitor 30. When high voltage defibrillation capacitor 30 is fully charged, the semiconductor switch 32 is activated to complete the circuit which delivers the charge of high voltage defibrillation capacitor 30 to the cardiac electrodes 35 for defibrillation or cardioversion of the heart. A configuration which is similar to the above circuit comprises substitution of an H-bridge in place of switch 32. This permits delivery of the current from high voltage defibrillation capacitor 30 in either polarity, which allows delivery of a biphasic pulse. It will be appreciated that numerous variations to the monitoring, control and capacitor configurations of circuit 10 are known in the art and are equally possible with the present invention, as shown for example in U.S. Pat. Nos. 5,199,429, 5,306,291, 5,312,443, 5,334,219 and 5,372,605.

Generally, circuit 10 works well in cardiac defibrillators; however, the SVO batteries have an energy storage density of only 500 joules per gram (J/g). This is due to the tradeoff between energy storage capability and current delivery capability. In contrast, the battery chemistry of the well known Lithium Iodide (LiI) pacemaker battery has approximately twice the energy storage density of the SVO battery, or about 750–1000 J/g. This means that implantable defibrillator devices using a SVO battery are utilizing a battery with a mass that is twice the mass required if a LiI pacemaker battery were used. Use of a LiI battery alone in an implantable defibrillator has not been possible because a LiI battery can delivery of only very small currents, on the order of milliamperes. As disclosed in U.S. Pat. No. 5,372,605, it is possible to solve this problem by using an LiI battery to power just the monitoring and integration circuits and related sub-systems, and using a separate SVO battery system to charge the high voltage defibrillation capacitor sub-system. Alternatively, power to the monitoring integration circuits and related sub-systems may be advantageously provided by a high-energy-density Li-Cfx battery.

Figure 2:
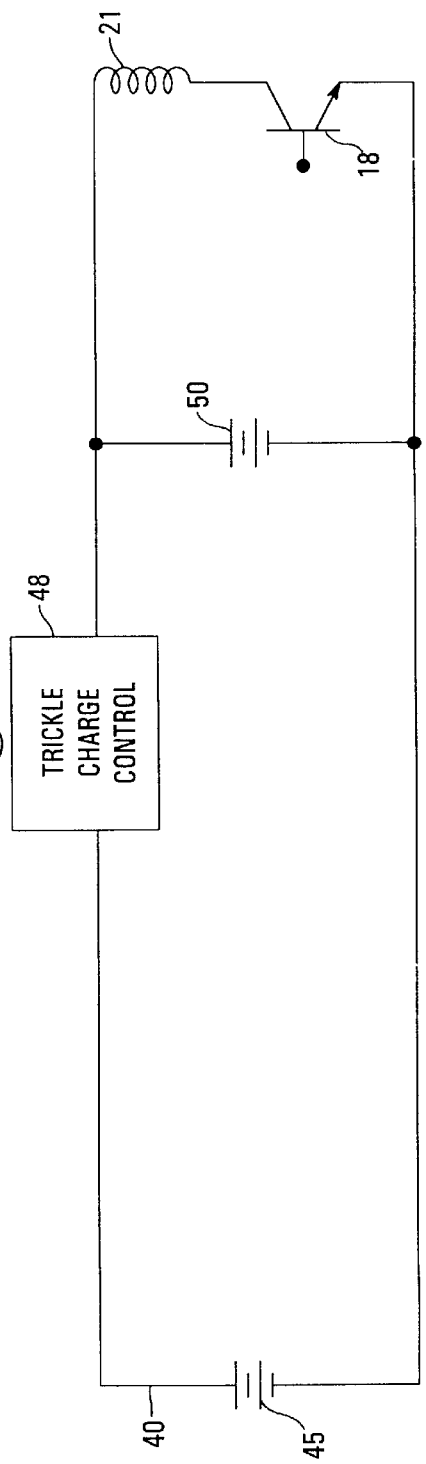
FIG. 2 is a simplified schematic circuit diagram of a staged energy concentration circuit.

FIG. 2 discloses a simplified schematic staged energy circuit 40. Circuit 40 comprises a first embodiment of an improved staged energy concentration means designed for replacing that portion of circuit 10 denoted as primary sub-circuit 42 in FIG. 1. Circuit 40 preferably comprises a first stage of energy concentration comprising a non-rechargeable battery, such as a high energy density pacing battery 45, configured for applying a small microampere current to the trickle charge control circuitry 48. Preferably, the first stage energy source 45 is capable of delivering at least one watt and the second stage energy concentration source 50 stores at least 15 joules. This provides an optimum current to be supplied to a second stage of energy concentration, comprising either a rechargeable battery 50 as discussed in reference to FIG. 2, or a low voltage, high energy density second stage concentration capacitor system 69 as discussed in reference to FIG. 5.

In the embodiment shown in FIG. 2, the rechargeable battery system preferably comprises a rechargeable defibrillator battery 50 that is maintained fully charged by the pacing battery 45. Rechargeable defibrillator battery 50 is used to drive primary 21 of the high voltage transformer, or similar power transfer means, through a switch 18 in a manner similar to conventional circuits, such as circuit 10.

The staged energy concentration configuration of circuit 40 permits use of high density pacing batteries to store energy in combination with a very small rechargeable defibrillator battery to deliver a high current for somewhere around 5 shocks. A typical defibrillator will deliver about 200 defibrillator shocks. Assuming each of the shocks is of 30 J, and assuming transformer losses of 25%, the energy system of a conventional implantable defibrillator must store at least 200×40 J=8000 J. Because all of this energy is stored in a single lower density SVO battery having an energy density of 500 J/gram, a total of at least 16 grams is required for battery system for a conventional defibrillator. Due to the staged energy arrangement of the present invention, the second stage energy concentration system need only store enough energy for a typical cardiac defibrillation session of about 5 shocks. As a result, the second stage of energy concentration must therefore only store about 5×40 J=200 J. In the embodiment of the rechargeable battery 50 as the second stage system, the 8000 J of energy can be stored in a high density LiI battery at 1000 J/g, for only about 8 grams with about an additional 1–2 grams required for the lower density rechargeable battery. Alternatively, a high-energy-density Li-CFx battery capable of storing up 1600 J of energy per gram of battery mass may be used as the second stage system. Using such a battery, is possible to store the needed 8000 J of energy in a mass of only about 5 grams, along with the additional 1–2 grams of mass needed for the lower density rechargeable battery.

A comparison of the characteristics of Li-CF$_x$ batteries relative to LiI batteries is presented below in Table 1.

TABLE 1

| Titanium Li-Cfx/Li-Iodine Comparison | | |
|---|---|---|
| | LiCFx | LiI |
| Deliverable Capacity (100 kΩ) | 1200 mAh | 1250 mAh |
| OCV | 3.3 V | 2.78 V |
| Pulse Amplitude (typical) | 20 mA | 100 µA |
| Impedance (1 kHz @ 0.9 Ah) | 6–7 Ω | ≈1000 Ω |
| Impedance (1 kHz @ 1.1 Ah) | <20 Ω | ≈4000 Ω |
| Weight | 7.6 g | 14.4 g |
| Volumetric Energy Density | 0.9 Wh/cc | 0.9 Wh/cc |
| Gravimetric Energy Density | 1600 J/g | 850–1000 J/g |
| Operating Temp. Range | −20 to +55° C. | 37° C. |
| Cell Swelling (typical) | <5% | 15 to 25% |
| Self-Discharge | <1%/yr | 2–4%/yr |

The total mass of the staged energy storage system of the present invention, when using the LiI battery discussed above as the first stage energy storage system cam offer significant advantages over current systems. For example, the total mass of such a system, comprising the mass of the LiI energy source (8 grams) and the mass of the second stage energy concentrator (1–2 grams), is not much more than one-half the mass of a conventional single stage energy storage system (16 grams). Even greater advantages can be realized through the use of the Li-CFx batteries also described above. The total mass of such a system would be on the order of 7 grams, including 5 grams for the Li-CFx battery, and 1–2 grams for the second stage concentrator, resulting in a savings of over half of the mass of current systems. Equally as important, the expense of the staged energy storage system of the present invention is significantly reduced as two SVO's are typically used for conventional energy storage in existing implantable defibrillators and the cost of a SVO battery that stores 4000 J is more than ten times that of a rechargeable battery or low voltage, high density capacitor system that could store the 200 J required for the second stage energy concentration required by the present invention. In addition to the LiI and Li-CF$_x$ batteries discussed above, other low current, high energy density batteries capable of providing significant advantages over SVO cells include radioisotope-activated batteries, such as shown in U.S. Pat. Nos. 3,767,947, 4,628,143 and 5,000,579, nuclear batteries, such as shown in U.S. Pat. Nos. 3,094,634, 3,740,273, 4,024,420 and 4,835,433, or thermoelectric batteries, such as shown in U.S. Pat. Nos. 4,002,497 and 4,026,726.

Although the amount of energy required to be stored by the second stage of energy concentration is relatively small, always less than 1000 J and typically less than 500 J, the second stage must be able to deliver a fairly high current of at least 0.5 A, and preferably about 1–2 A. Representative rechargeable battery chemistries having single battery cells that are capable of meeting these specifications for high current delivery are shown in Table 2, below.

TABLE 2

SECOND STAGE BATTERIES

| Chemistry | Average Cell Voltage |
|---|---|
| LiMoS$_2$ | 1.85 |
| LiMnO$_2$ | 3.0 |
| LiV$_2$O$_5$ | 2.8 |
| LiTiS$_2$ | 2.2 |
| LiV$_6$O$_{13}$ | 2.3 |
| LiCuC$_{12}$ | 3.2 |
| LiSO$_2$ | 3.1 |
| NiCad | 1.2 |
| Alkaline | 1.5 |
| Lead acid | 2.0 |

FIG. 3 discloses another embodiment of the staged energy concentration invention. Circuit 60 discloses a single cell pacing battery 63 which is used to power a voltage doubler circuit 67. This doubler circuit 67, which comprises numerous embodiments as described, for example, in U.S. Pat. No. 5,372,605, may be configured to produce an output of approximately 6 volts for charging a rechargeable defibrillation battery, such as battery 70.

Another embodiment of a staged energy concentration defibrillator circuit is shown in FIG. 4, in which circuit 76 comprises first stage battery 80. Battery 80 is a low voltage, for example a 2.8 volt, LiI single cell battery which charges two second stage batteries 83 and 84. Batteries 83, 84 are preferably Lithium Titanium Disulfide (LiTiS$_2$) batteries. Preferably, battery 84 is charged through diode 86, battery 83 is charged through diode 87, and resistor 89 is used with a preferred value of 10K ohms. Field effect transistor switch 92 is off during this time. It is recognized that this schematic circuit is further simplified because there is optimal trickle charge current limiting between battery 80 and the two diodes 86, 87; however, that detail is not considered important to this depiction of the invention.

When fibrillation is detected by related detection circuitry, it is then time to charge the defibrillation capacitor(s) and switch 92 is turned on. That places batteries 83 and 84 in series, providing a voltage of approximately 5 volts for the transformer primary 21. As above, oscillating switch 18 is used to cause a pulsating current to pass through primary 21 of the transformer.

Use of a multi-stage energy storage system, as disclosed in the present invention, provides great savings in both volume and weight of an implantable biomedical device. For example, because the existing defibrillator battery chemistry has about half the density of the pacing battery, it is possible to reduce the total battery weight of an implantable cardioverter defibrillator by greater than about 50% by allowing for the use of a higher energy density battery as the primary energy storage system and relying on the second stage energy concentration as taught by the present invention to actually charge the defibrillation capacitors of the implantable cardioverter defibrillator. This provides dramatic improvement in the manufacture, implantation, and operation of the defibrillator, particularly in view of the restricted size of desired pectoral implant sites.

In either configuration, it is advantageous to provide a rechargeable second stage concentration that permits rapid charging of the defibrillator capacitor means. Indeed, in certain configurations it is possible to recharge at a rapid 3–5 second rate using the two stage charging system of the present invention, rather than at a slower rate of 12–15 seconds which is common in the industry. Therefore, yet another advantage of this invention derives from the use of the second stage energy concentration as a recharge rate accelerator. This also results in a defibrillator with reduced end of life charge degradation due to the constantly recharged second stage. This feature effectively provides a battery life extension capability before elective replacement, assuming certain accepted energy levels.

Figure 5:
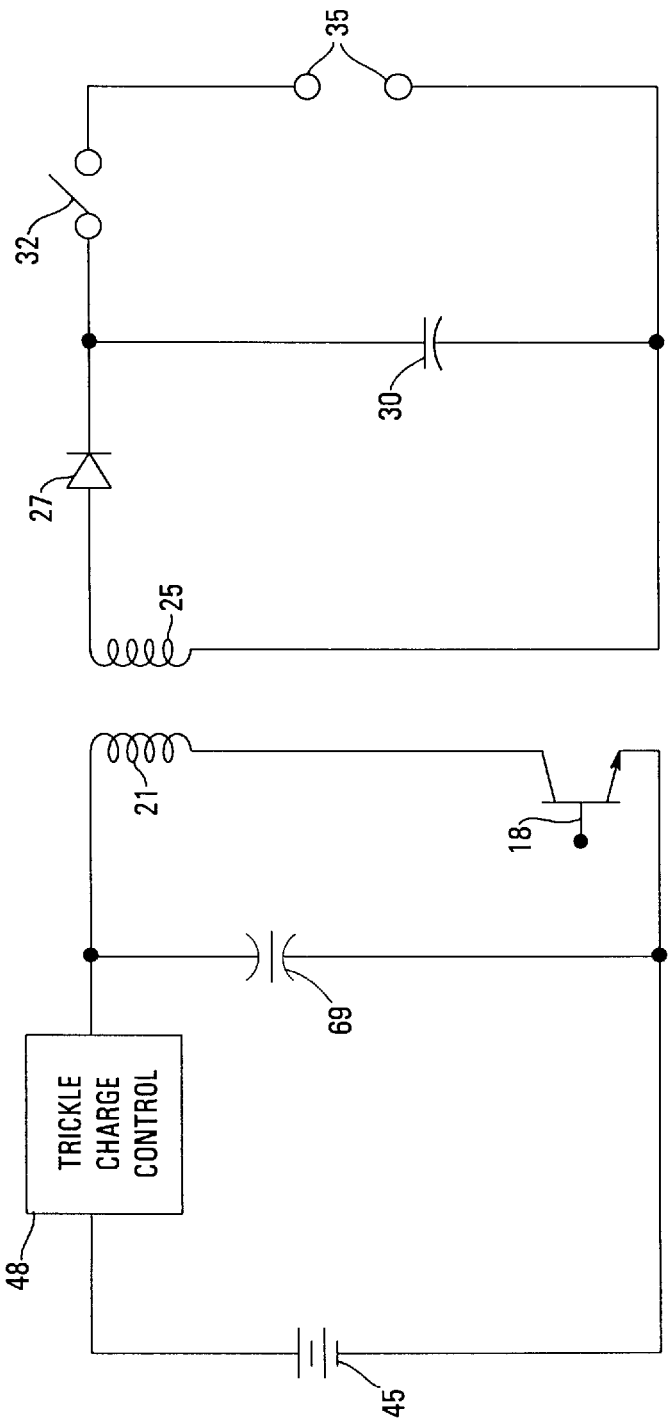
FIG. 5 is a simplified schematic circuit diagram of a staged energy concentration circuit using a concentration capacitor system.

In the embodiment shown in FIG. 5, a low voltage, high energy density second stage concentration capacitor system 69 is used in place of rechargeable defibrillation battery 50 as shown in FIG. 2. Second stage concentration capacitor system 69 is used to drive the primary coil 21 of high voltage transformer 15 through the use of oscillator driven switch 18. The secondary side 25 of high voltage transformer 15 charges defibrillation capacitor 30 through the rectifying diode 27. The remaining portion of circuit 40' operates in a manner similar to circuit 10 as described in FIG. 1.

As with FIG. 5, a trickle charge control circuit 48 controls the charging of concentrations capacitor system 69 from non-rechargeable battery 45. Trickle charge control circuit 48 is of conventional design and may include a voltage step-up feature as described for example, in U.S. Pat. No. 5,372,605. The voltage step-up feature is preferably included to counteract a decrease in the efficiency of high voltage transformer 15 at lower voltages as concentration capacitor system 69 discharges. For example, if non-rechargeable battery 45 is a 2.2 V LiI battery, trickle charge control circuit 48 would include a 5×1 voltage step-up to yield a total of 11 V across concentration capacitor system 69. As a result, 75% of the energy transfer from concentration capacitor system 69 to high voltage transformer 15 will occur at a voltage of 5.5 V or higher. Alternatively, a single SVO 3.0 V cell could be used with a 4×1 voltage step-up, for example. In the former case with the LiI battery, the resulting energy storage system would have more total stored energy (8000 J), but would take several hours to fully recharge concentration capacitor system 69 after delivery of a complete set of countershocks. In the later case with the SVO battery, the resulting energy storage system would have less total stored energy (4000 J), but would be able to quickly recharge concentration capacitor system 69 in less than a minute. Because the concentration capacitor system 69 would serve as buffer to maintain optimum transfer characteristics across high voltage transformer 15, the later example would have the significant advantage of saving the cost of a second SVO cell, as compared to energy storage systems for existing implantable cardioverter defibrillators.

An alternative embodiment of the later case would allow concentration capacitor system 69 to be used together with the SVO battery and the 4×1 voltage step up to jointly produce the voltage across primary coil 21 of high voltage transformer 15. It would be possible, for example, to make a single cell SVO battery arrangement more efficient if, instead of trying to take all 30 J from the SVO cell, 15 J was taken from the SVO cell through the step up circuit and the other 15 J was taken from 30 J stored in two dual layer capacitors. Total net energy requirements for such a system would be 8 grams for the SVO cell and 4 grams for the dual layer caps occupying only an additional 3 cc. Alternatively, the dual layer capacitors could be used provide power to the circuitry of the implantable cardioverter defibrillator while the SVO cell is charging the main energy delivery capacitor. In this arrangement, the use of a single dual layer capacitor would prevent undesirable low voltage spikes from resetting the internal circuitry of the implantable cardioverter defibrillator during the charging of the main energy capacitor.

Second stage concentration capacitor system 69 is preferably comprised of one or more double layer capacitors having no permanent dielectric, although it would be possible to use an electrolytic capacitor, provided the electrolytic capacitor had a sufficient energy density rating. Currently available capacitor technology is capable of producing a double layer capacitor with a maximum voltage rating of 11 volts and a maximum energy density of around 10.7 J/cc. An example of such a double layer capacitor is the Panasonic SG. Other possible dual layer capacitors useful with the present invention include the Ruthenium Oxide (RO) dual layer capacitor developed by Pinnacle Research Co. New manufacturing technologies and materials are being introduced for double layer capacitors which have the potential to increase the capacitance and voltage ratings of these devices. These improvements involve new materials with increased surface areas (which directly relates to capacitance), and new manufacturing techniques to reduce the space between the plates which decreases both the overall resistance and the overall size of the capacitor.

Using the example previously set forth, assume that the implantable cardioverter defibrillator must be capable of delivering 5 countershocks, each of 30 J. In the case of the concentration capacitor system 69 as the second stage system, only one-half of the electrical voltage found in the capacitor system will occur across the load (in this case the primary coil 21 of high voltage transformer 15) assuming maximum energy transfer conditions exist due to load matching between the capacitor system and the load. As a result, when the concentration capacitor system 69 is used as the second stage system of the present invention, it must store 5×80 J=400 J for operation equivalent to rechargeable battery 50.

A set of calculations can be established to determine, for a given delivered energy/countershock and number of countershocks/therapy regimen, the appropriate configuration for concentration capacitor system 69. Because of the 50% loss for load matching and the 25% loss across transformer 15, the energy required ($E_{req}$) for second stage concentration capacitor system can be stated as follows:

$$E_{req}=((E_{del}/L_{tran})/L_{load})*N \qquad (1)$$

where $E_{del}$ is the desired maximum energy to be delivered by a countershock, $L_{tran}$ is the 1/transformer efficiency, $L_{load}$ is 1/loss due to load matching and N is the desired number of countershocks in a therapy regimen. Assuming that the individual dual layer capacitors that makeup concentration capacitor system 69 are arranged in series, then:

$$V_{tot}=V_1+V_2+ \ldots V_n=V*n \qquad (2)$$

$$1/C_{tot}=1/C_1+1/C_2+ \ldots 1/C_n=1/C*n \qquad (3)$$

$$ESR_{tot}=ESR_1+ESR_2+ \ldots ESR_n=ESR*n \qquad (4)$$

For a capacitive discharge energy transfer, assuming no losses, the delivered energy is given by the classic equation:

$$\begin{aligned}E_{del} &= .5*C*V^2 \\ &= .5*C/n*(V*n)^2\end{aligned} \qquad (5)$$

solving Eq. (5) for the number (n) of dual layer capacitors required for a given delivered energy yields:

$$n=(2*E_{del})/(C*V^2) \qquad (6)$$

using Eqs. (1) and (6) to solve for the number (n) of dual layer capacitors required for a given delivered energy, transformer efficiency, load loss and therapy regimen yields:

$$n=(2*N*E_{del})/(L_{tran}*L_{load}*C*V^2) \qquad (7)$$

Substituting for a 40 J countershock, a 75% transformer efficiency, a 50% load efficiency and a 5 countershock therapy regimen into Eq. (7) and solving, for example, for the dual layer Panasonic SG capacitors, each having ratings of:

```
Capacitance = 1 F
Voltage     = 5.5 V
ESR         = 30 Ω
Volume      = 1.42 cc
Weight      = 2 grams
E_std       = 15.25 J
``` the minimum number (n) of such dual layer capacitors required would be 27. While this large number of capacitors for existing dual layer capacitors does not make such an arrangement a particularly attractive alternative to energy supply systems for existing implantable devices, there are other arrangements which do make the concentration capacitor system 69 an attractive alternative. For example, when a SVO battery is used, the number of countershocks in a therapy regimen can be reduced to 1 because the battery can recharge concentration capacitor system 69 between countershocks. As such, the total number of such capacitors required would be only 6, a realistic tradeoff even with existing dual layer capacitor technology to reduce the cost of the implantable device. Alternative, if the effectiveness of the countershock waveform is increased so that the maximum delivered energy/countershock can be decreased to, for example, 16 J, then the total number of capacitors required would be cut in half. This value could be reduced still further if the therapy shock regimen were set to a smaller value than 5 shocks.

An excellent example of a prophylactic implantable cardioverter defibrillator which could take advantage of arrangements similar to those described in the previously identified co-pending application entitled "PROPHYLACTIC IMPLANTABLE DEFIBRILLATOR". For example, a prophylactic implantable defibrillator with a total energy budget of 4000 J could be provided with a three-shock therapy regimen for a budgeted number of 50 regimen cycles, each of the countershocks in a therapy regimen cycle having a maximum delivered energy of 10 J, 10 J and 20 J, respectively. In this situation, the total energy required to be stored in concentration capacitor system 69 would be about 105 J, an energy level which can be achieved by 7 individual dual layer capacitors utilizing existing capacitor technology, that together would occupy about 9.75 cc and weigh about 14 grams. When combined with a 4000 J single cell LiI battery (4 cc and 8 grams), the overall volume of the energy storage system for this prophylactic defibrillator (total volume <13 cc) is somewhat less than existing volumes of 16 cc for dual cell SVO battery systems, and the mass (total mass <18 grams) is almost one-half of the mass for a 32 gram dual cell SVO battery system. Most importantly, however, the cost of such an energy storage system for an implantable device will decrease from almost $1000 to less than $50.

What is claimed is:

1. An implantable defibrillator for delivering high voltage electrical pulses to a plurality of implantable electrodes within a human patient for treating cardiac arrhythmias, comprising:

monitor circuitry that detects the occurrence of a cardiac arrhythmia in the human patient;

a charge storage system that stores a high voltage electrical output pulse to be delivered to the implantable electrodes;

control circuitry operably connected to the monitor circuitry and the charge storage system to control the charging and discharging of the charge storage system in response to the cardiac arrhythmia; and a power source system including a low voltage battery system operably connected to the monitor circuitry and the control circuitry to provide power thereto and a low voltage rechargeable energy storage system operably connected to a transformer to provide the power for the charge storage system.

2. The implantable defibrillator of claim 1 wherein the battery system provides a long-term, low-voltage, low-current source having an electrical current of less than 10 milliamperes.

3. The implantable defibrillator of claim 1 further comprising a trickle charge system electrically connected between the battery system and the energy storage system to constantly recharge the energy storage system.

4. The implantable defibrillator of claim 1 wherein the energy storage system can charge the charge storage system to a maximum charging voltage in less than 6 seconds.

* * * * *